(12) United States Patent
Hong et al.

(10) Patent No.: US 9,447,012 B2
(45) Date of Patent: Sep. 20, 2016

(54) SYNTHETIC PROCESS OF ADIPIC ACID

(71) Applicants: HYUNDAI MOTOR COMPANY, Seoul (KR); SNU R&DB FOUNDATION, Seoul (KR)

(72) Inventors: Chae Hwan Hong, Seoul (KR); Young Gyu Kim, Gunpo-si (KR); Nara Shin, Seoul (KR)

(73) Assignees: HYUNDAI MOTOR COMPANY, Seoul (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/676,657

(22) Filed: Apr. 1, 2015

(65) Prior Publication Data

US 2016/0168065 A1 Jun. 16, 2016

(30) Foreign Application Priority Data

Dec. 10, 2014 (KR) .................. 10-2014-0177803

(51) Int. Cl.
*C07C 51/09* (2006.01)
*C07C 67/297* (2006.01)
*C07C 51/42* (2006.01)

(52) U.S. Cl.
CPC ............... *C07C 51/09* (2013.01); *C07C 51/42* (2013.01); *C07C 67/297* (2013.01)

(58) Field of Classification Search
CPC ...... C07C 51/09; C07C 55/14; C07C 51/377
See application file for complete search history.

(56) References Cited

U.S. PATENT DOCUMENTS

| 4,792,620 A * | 12/1988 | Paulik .................. B01J 31/0231 560/232 |
| 8,241,879 B2 | 8/2012 | Picataggio et al. |
| 8,343,752 B2 | 1/2013 | Picataggio et al. |
| 2013/0157343 A1 | 6/2013 | Picataggio et al. |

FOREIGN PATENT DOCUMENTS

| KR | 1020030012426 A | 2/2003 |
| WO | 95/07996 A1 | 3/1995 |
| WO | 2010/0144862 A2 | 12/2010 |

OTHER PUBLICATIONS

Shiramizu et al, Angewandte Chemie International Edition, Expanding the Scope of Biomass-Derived Chemicals through Tandem Reactions Based on Oxorhenium-Catalyzed Deoxydehydration 2013, 52, pp. 12905-12909 with Supporting Data pp. 1-35.*
Li et al, Angewandte Chemie International Edition, Highly Efficient Chemical Process to Convert Mucic Acid into Adipic Acid and DFT Studies of the Mechanism of the Rhenium-Catalyzed Deoxydehydration, 2014, 53, pp. 4200-4204.*
White et al, Basic Energy Sciences Advisory Committee Subpanel Workshop Report, Opportunities for Catalysis in the 21st Century, 2002, pp. 1-47.*
Moon, T. S. et al., "ERRATUM: Production of Glucaric Acid from a Synthetic Pathway in Recombinant *Escherichia coli*," Applied and Environmental Microbiology, Feb. 2009, vol. 75, No. 13, pp. 589-595 with cover page.
Li, X. et al. "Highly Efficient Chemical Process to Convert Mucic Acid into Adipic Acid and DFT Studies of hte Mechanism of the Rhenium-Catalyzed Deoxydehydration," Angewandte Communications; Angew. Chem. Int. Ed. 2014, 53, pp. 4200-4204.
Li, Xiukai et al., "Highly Efficient Chemical Process To Convert Mucic Acid into Adipic Acid and DFT Studies of the Mechanism of the Rhenium-Catalyzed Deoxydehydration", Angewandte Chemie, Apr. 14, 2014, vol. 126, Issue. 16, pp. 4284-4288, with supporting documents.

* cited by examiner

*Primary Examiner* — Paul A Zucker
(74) *Attorney, Agent, or Firm* — McDermott Will & Emery LLP

(57) ABSTRACT

A process for synthesizing adipic acid comprising the steps of using glucaric acid or galactaric acid as a starting material, using rhenium catalyst and acid catalyst, using one or more reaction solvents selected from a group consisting of heptanol and butanol; and b) subjecting glucaric acid ester or galactaric acid ester obtained from the step a) to hydrogenation reaction with precious metal catalyst, and then hydrolyzing the ester obtained from this reaction to obtain adipic acid.

13 Claims, 18 Drawing Sheets

SYNTHETIC PROCESS OF ADIPIC ACID

CROSS REFERENCE TO RELATED APPLICATION

The present application claims the benefit of priority to Korean Patent Application Number 10-2014-0177803 filed on Dec. 10, 2014, the entire contents of which application are incorporated herein for all purposes by this reference.

TECHNICAL FIELD

The present disclosure relates to a novel synthetic process of adipic acid with a variety of uses including as a source material for nylon which can be used for automobile engine sash injection units.

BACKGROUND

Owing to continuous increases in population and industrial development, oil is now the starting material for 95% of chemical products, and has become one of humanity's most important natural resources.

However, oil deposits are limited and there are many environmental issues associated with exploiting oil deposits. Thus, it is important to develop alternative solutions, and as a consequence, there are many investigations researching alternative materials to oil resources. In this regard, biomass (derived from plant resources such as corn, sugarcane, ligno(wood)-plant resources, palm, and algae), which is naturally produced, renewable, and environmentally (eco-) friendly, is regarded as an important potential resource for oil substitutes.

The automobile industry is closely associated with oil resources, and the importance of biomass-related research and development as future resources for the automobile industry is increasing.

Despite small industrial scale and lower economic efficiency than petrochemical material of biomass, recent report by Utretcht University (according to a request of European bio-plastic association and EPNOE (European Polysaccharide Network of Excellence)) expects that the usage of biomaterials will rapidly increase ten (10) years from now, and that up to 90% of petrochemical materials can be substituted with biomaterials. Examples of inner/outer injection unit materials currently used in the automobile industry include polypropylene, nylon, polycarbonate and Acrylonitrile butadiene styrene (ABS). Of the above materials, polypropylene is the most commonly used, and nylon is the second most commonly used (about 15 kg per automobile). Therefore, if the manufacturing technology for nylon were converted into that based on biomass, it is expected that considerable ripple effect would occur. As such, many research projects for biomass-based nylon materials are underway.

Among the various nylon materials, there is great demand for nylon 66 as well as nylon 6 because of their superior properties, but the manufacturing technology from biomass resources has not yet been established. Once manufacturing technology for nylon 66 has been developed, it is expected to have a huge effect in terms of both economic and environmental aspects.

Nylon 66 is used for automobile parts that can withstand high temperature because of its excellent heat resistance, abrasion resistance, and chemical resistance. After nylon 6, it is the most frequently used nylon for automobiles. Nylon 66 is prepared by the dehydration condensation reaction of hexamethylenediamine and adipic acid. Monomeric adipic acid for nylon 66 synthesis is produced via a chemical synthetic process using cyclohexanone derived from benzene which is obtained in the purification process of crude oil.

However, the above manufacturing technology and process have many problems such as oil price instability, the usage of toxic compounds such as benzene, and the formation of environmental pollutants including $NO_X$. Thus, there is a need to substitute this current manufacturing technology with biomass technology. Accordingly, nylon production using biomass will decrease oil dependency and reduce the formation of environmental pollutants.

In the nylon 66 production using biomass, synthesizing adipic acid for the nylon 66 monomer from biomass is considered the most important step. However, this technology remains at the research and development (R&D) stage, and has not yet been commercialized. In addition, technologies for synthesizing adipic acid from glucose or galactose have not yet been disclosed, though there are several patents using glucaric acid as an intermediate for adipic acid synthesis.

Specifically, a method for preparing D-glucaric acid derived from green algae has been applied. D-glucaric acid is prepared using green algae-derived sugar, and specifically, D-glucuronic acid is converted from primitive forms of green algae into D-glucaric acid by using a recombinant microorganism transfected with the D-glucaric acid production gene. This method comprises steps of (i) drying and milling green algae to form green algae particles; (ii) hydrolyzing the green algae powder with an acid catalyst to obtain monosaccharide; and (iii) converting the monosaccharide into D-glucaric acid by fermentation with a recombinant microorganism having the D-glucaric acid production gene. Here, a novel fermentation process for preparing a chemical product with enormous industrial utility by using green algae resources, but it has not been implemented on an industrial scale. The process is very complicated because it uses metabolic engineering technology for glucaric acid production by utilizing (i) saccharification technology to prepare monosaccharide from primitive forms of green algae and (ii) a recombinant microorganism for the production of glucaric acid.

Other research regarding D-glucaric acid production from biomass includes Moon, T. S. et al. (Moon, T. S. et al. (2009) Appl. Environ. Microbiol. 75: 589-595), which discloses a method for D-glucaric acid production using D-glucose as raw material.

In the above method, D-glucaric acid is prepared via a complex chain enzymatic reaction in *Escherichia coli* by using PPS (phosphoenolpyruvate synthase), myo-inositol-1-phosphate synthase, phosphatase, myo-inositol oxygenase, and urinatedehydrogenase. This is a very complicated synthesis, and efficiency with the glucose input is very low (yield: 17.4% or less).

Further, a biological method for preparing adipic acid and adipic acid from renewable fatty acids and a genetically modified microorganism such as yeast has been developed.

Genetic modification for adipic acid production with high yield for preparing adipic acid in which genetically modified yeast comprises PDX5 polypeptide wherein PDX4 polypeptide or its promotor, FAT1 polypeptide or its promotor and ACS1 polypeptide gene are removed, and a method for producing adipic acid from fatty acid resources via fermentation have been studied.

However, the above technologies are much more complicated than chemical synthetic methods, and their costs are very high.

Under the above circumstances, the present disclosure describes a novel synthetic method which can simply and economically provide adipic acid from biomass such as plant or marine resources. Further, the present disclosure describes a method comprising preparing glucaric acid or galactaric acid as an intermediate from glucose or galactose derived from plant or marine resources, and then reducing this intermediate to form adipic acid, providing a bio-adipic acid synthesis with a simple and eco-friendly process and a low cost, thereby completing the present disclosure.

SUMMARY

In order to overcome the above-mentioned problems, the present disclosure is intended to provide a process for efficiently synthesizing bio-adipic acid, a monomer of nylon 66, with glucaric acid or galactaric acid as a starting material, which is derived from glucose or galactose from biomass by a catalytic reduction reaction.

An aspect of the present inventive concept provides a novel synthesizing process for adipic acid.

According to an embodiment of the present disclosure, a synthetic process for adipic acid includes a) adding glucaric acid or galataric acid as a starting material, rhenium catalyst, and acid catalyst to one or more reaction solvents selected from the group consisting of heptanol and butanol; and b) subjecting the intermediate obtained from step a) to a hydrogenation reaction with a precious metal catalyst, and then hydrolyzing the ester obtained from this reaction of this reaction to obtain adipic acid.

DETAILED DESCRIPTION

Figure 1:
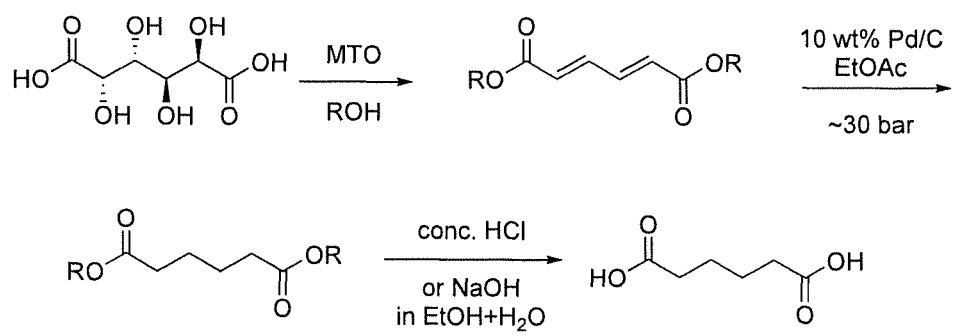
FIG. 1 shows a reaction scheme when using galactaric acid as a starting material according to the present disclosure.
Figure 2:
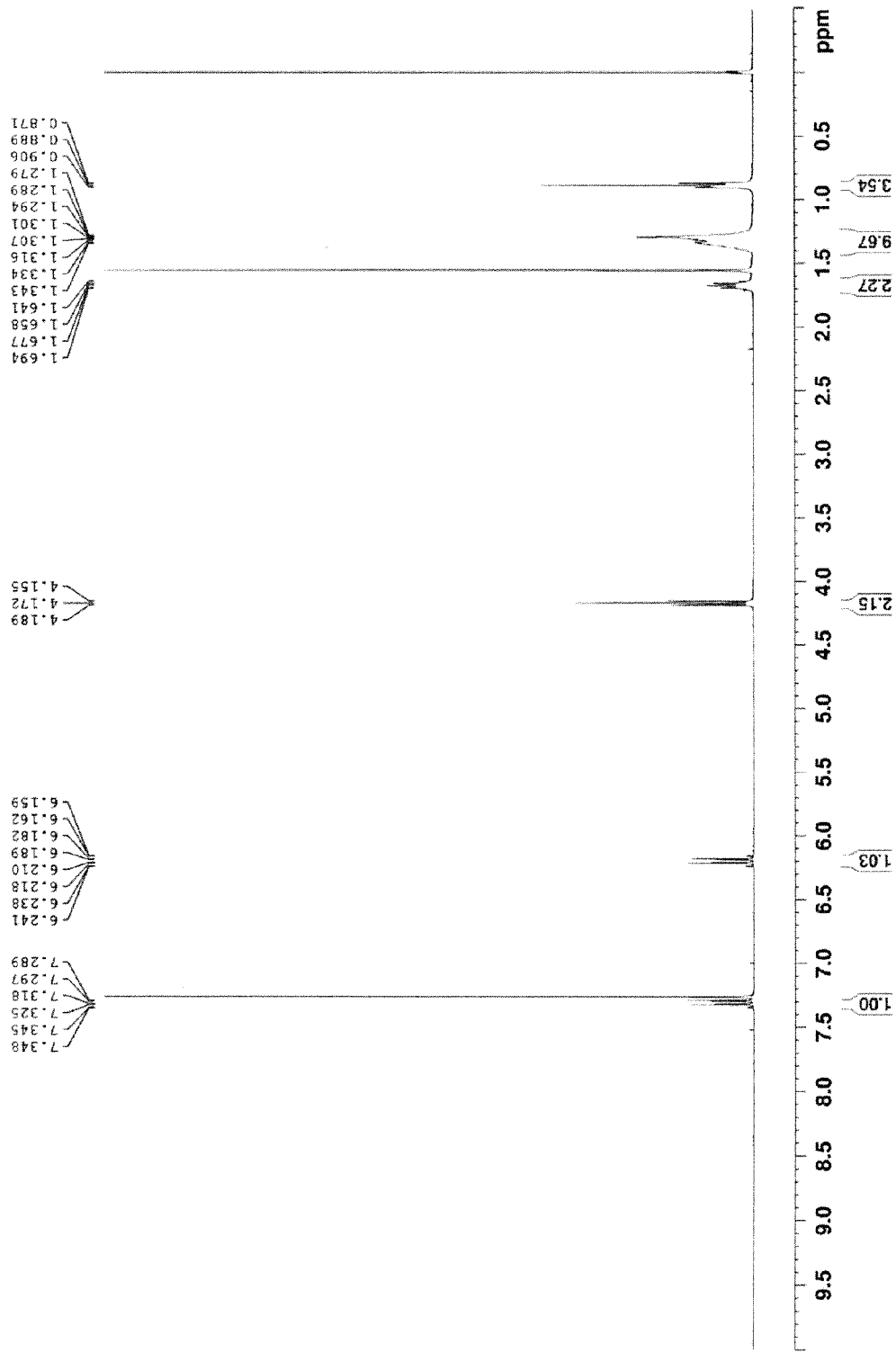
FIG. 2 shows $^1$H NMR data of diheptylgalactarate obtained in Example 1.
Figure 3:
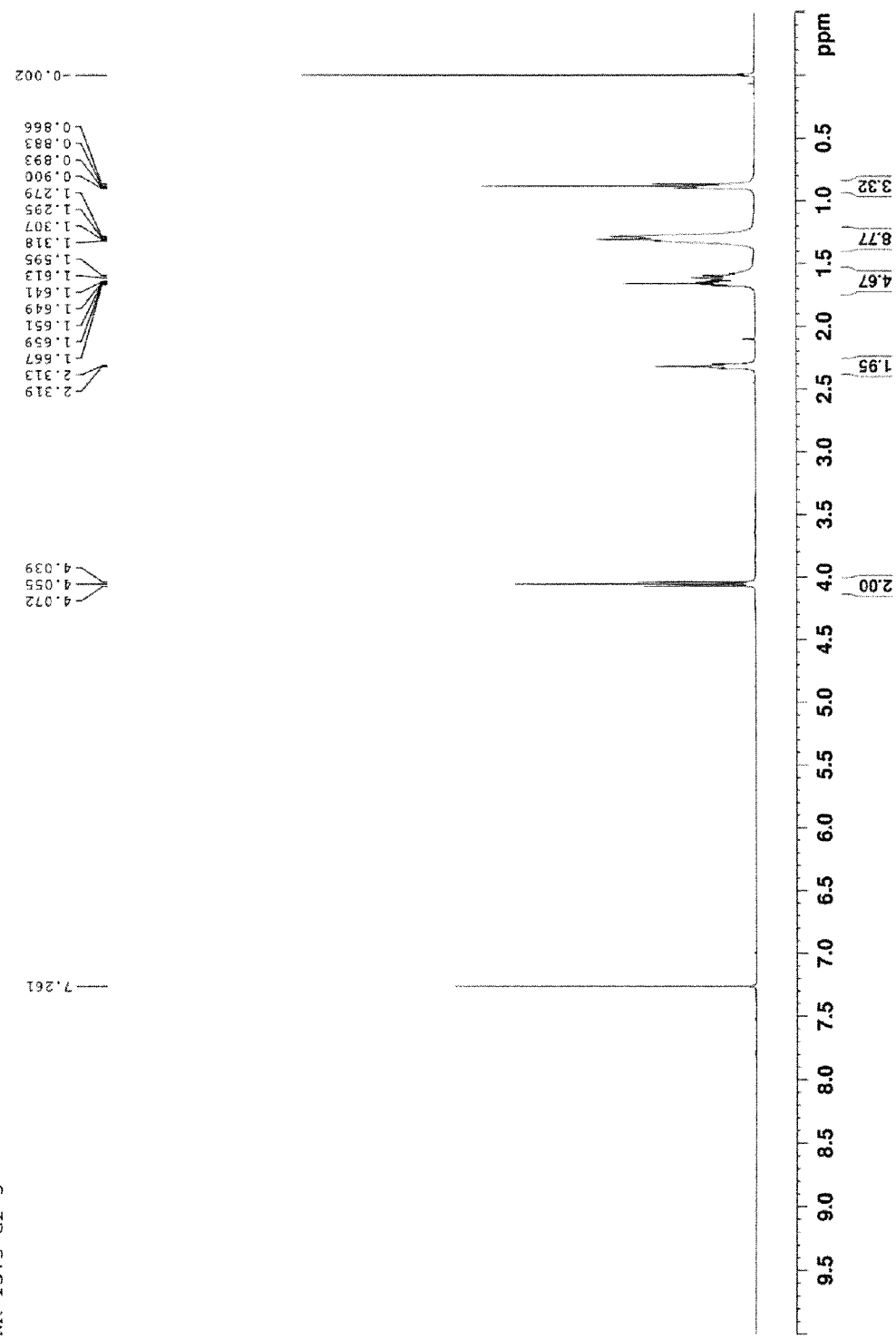
FIG. 3 shows $^1$H NMR data of diheptyladipate obtained in Example 1.
Figure 4:
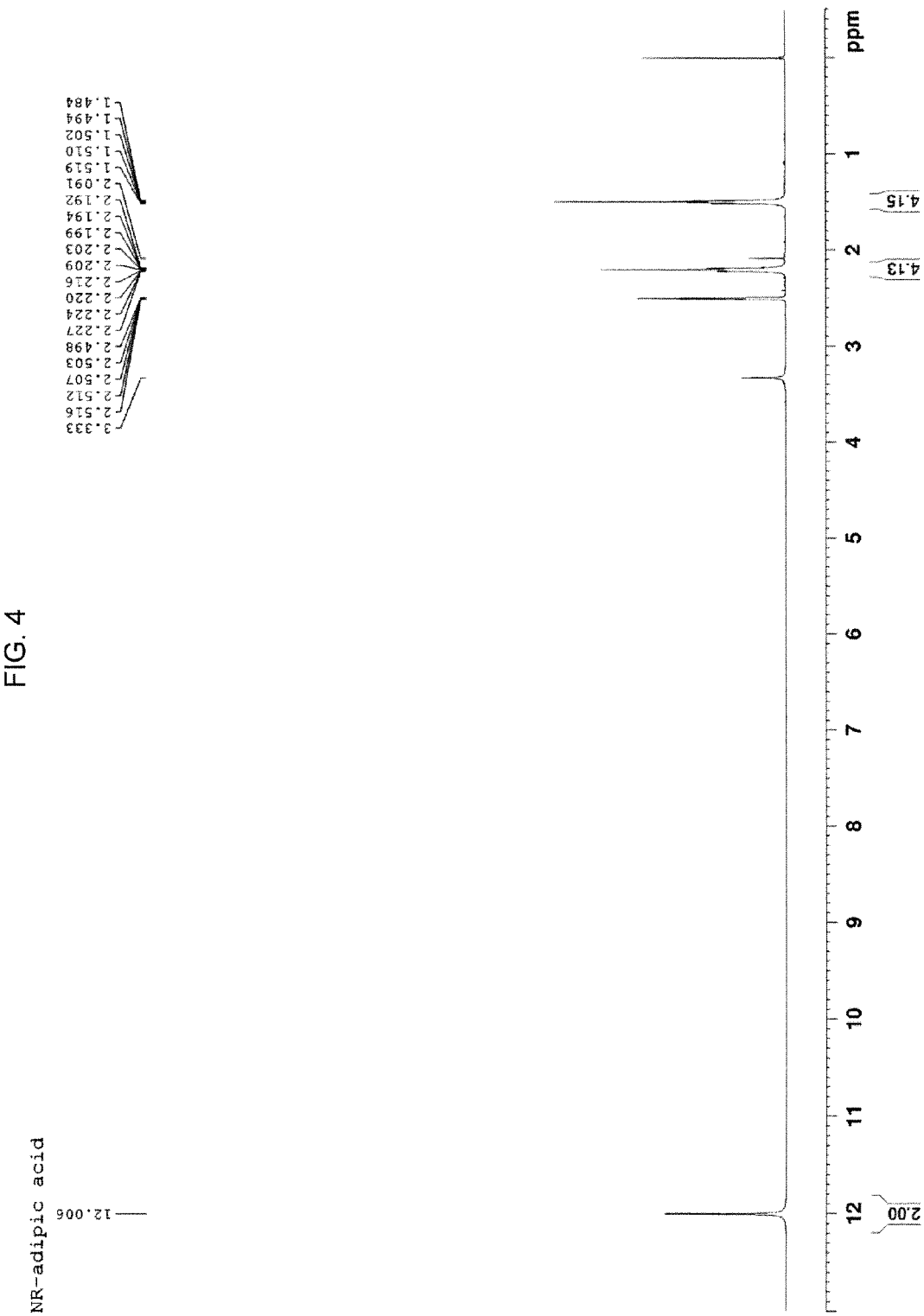
FIG. 4 shows $^1$H NMR data of adipic acid obtained in Example 1.
Figure 5:
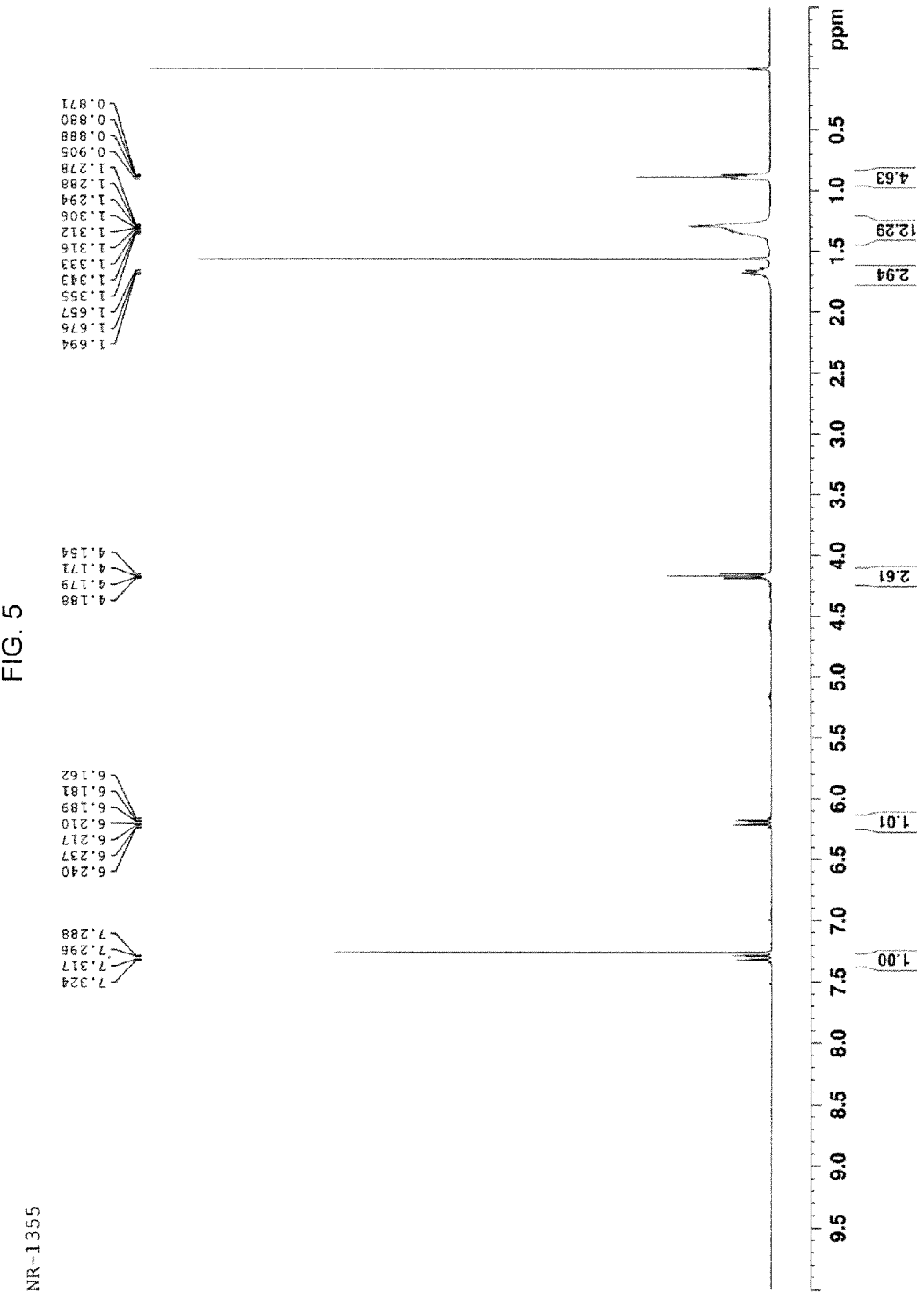
FIG. 5 shows $^1$H NMR data of diheptylgalactarate obtained in Example 2.
Figure 6:
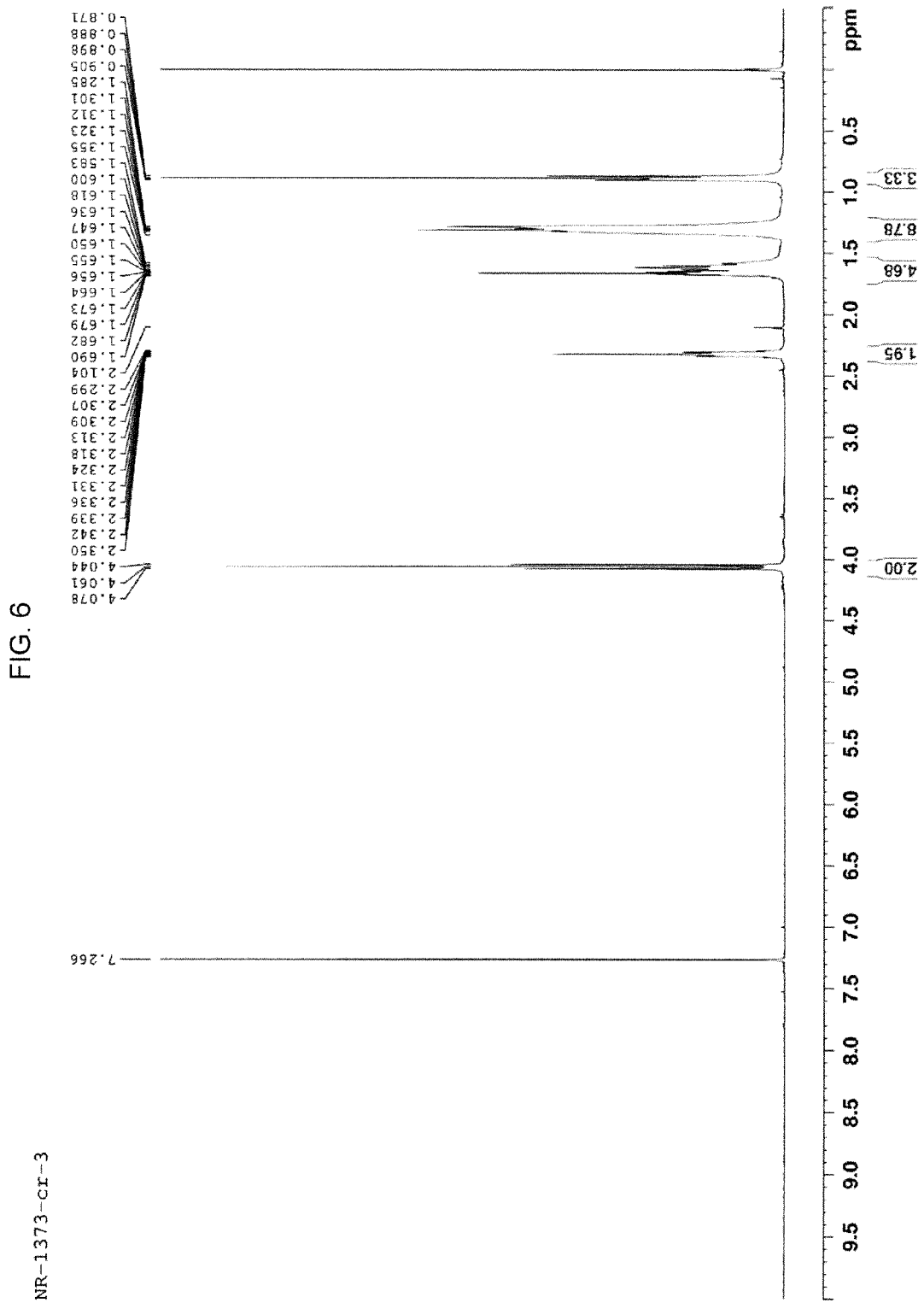
FIG. 6 shows $^1$H NMR data of diheptyladipate obtained in Example 2.
Figure 7:
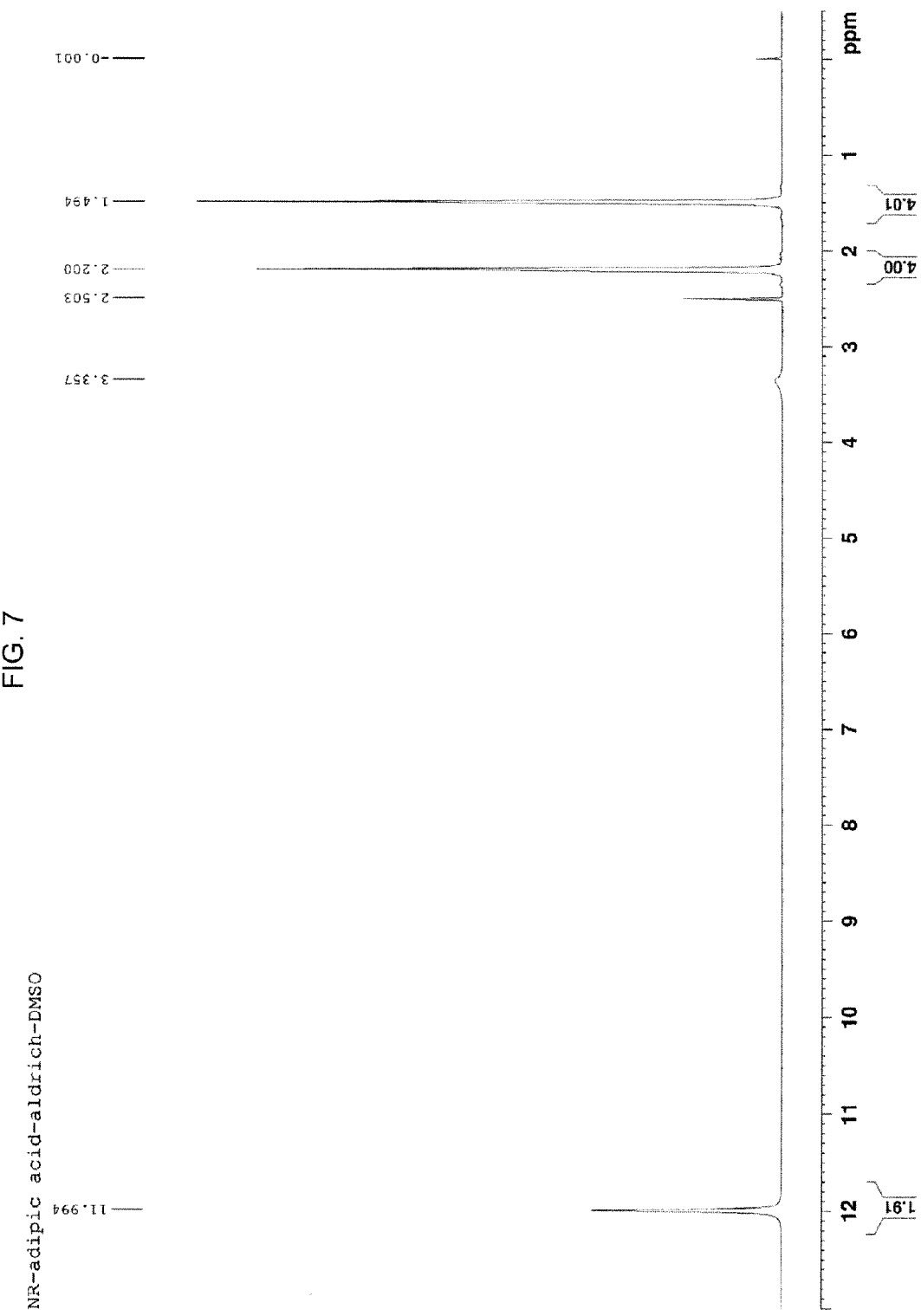
FIG. 7 shows $^1$H NMR data of adipic acid obtained in Example 2.
Figure 8:
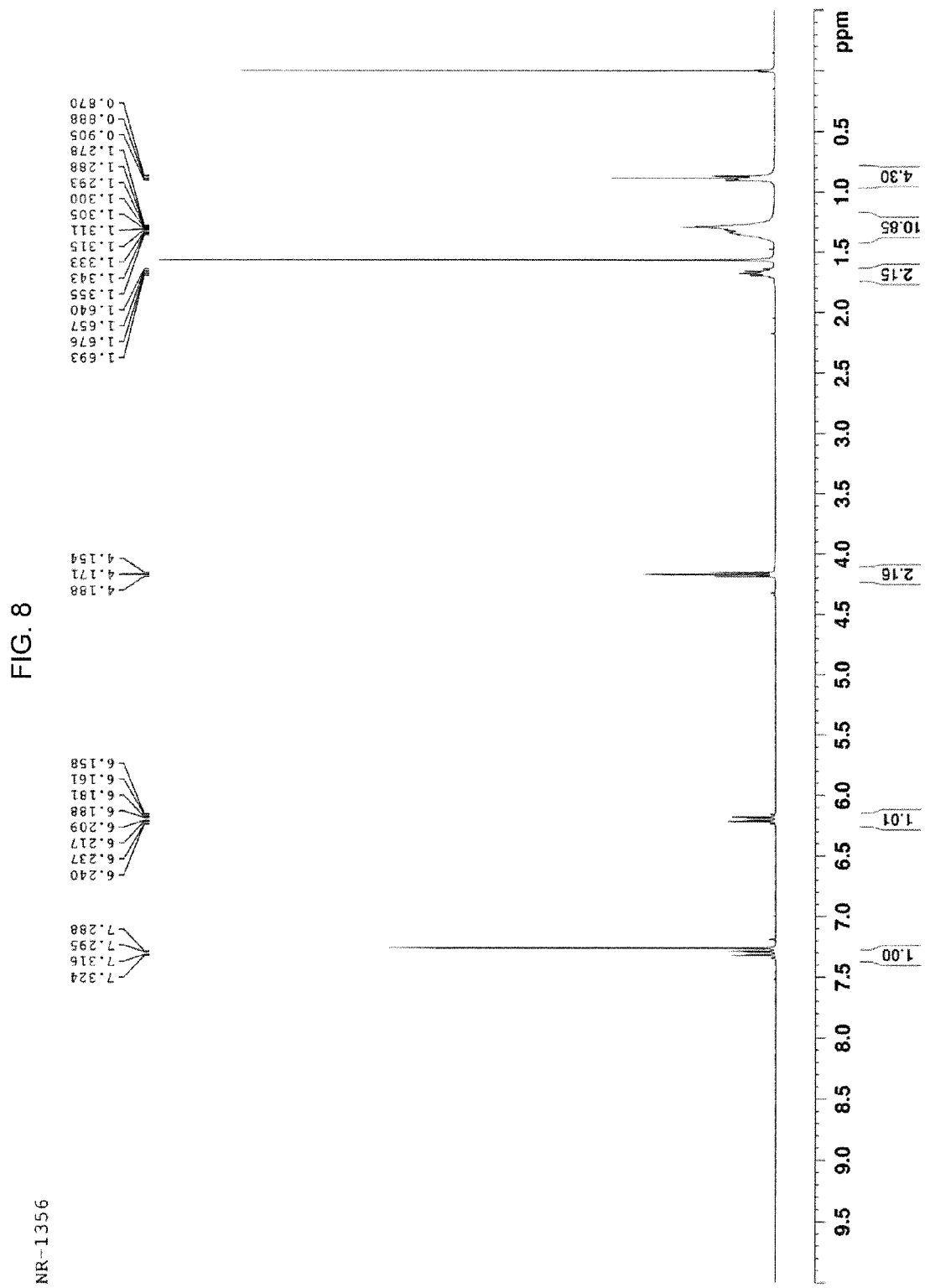
FIG. 8 shows $^1$H NMR data of diheptylgalactarate obtained in Example 3.
Figure 9:
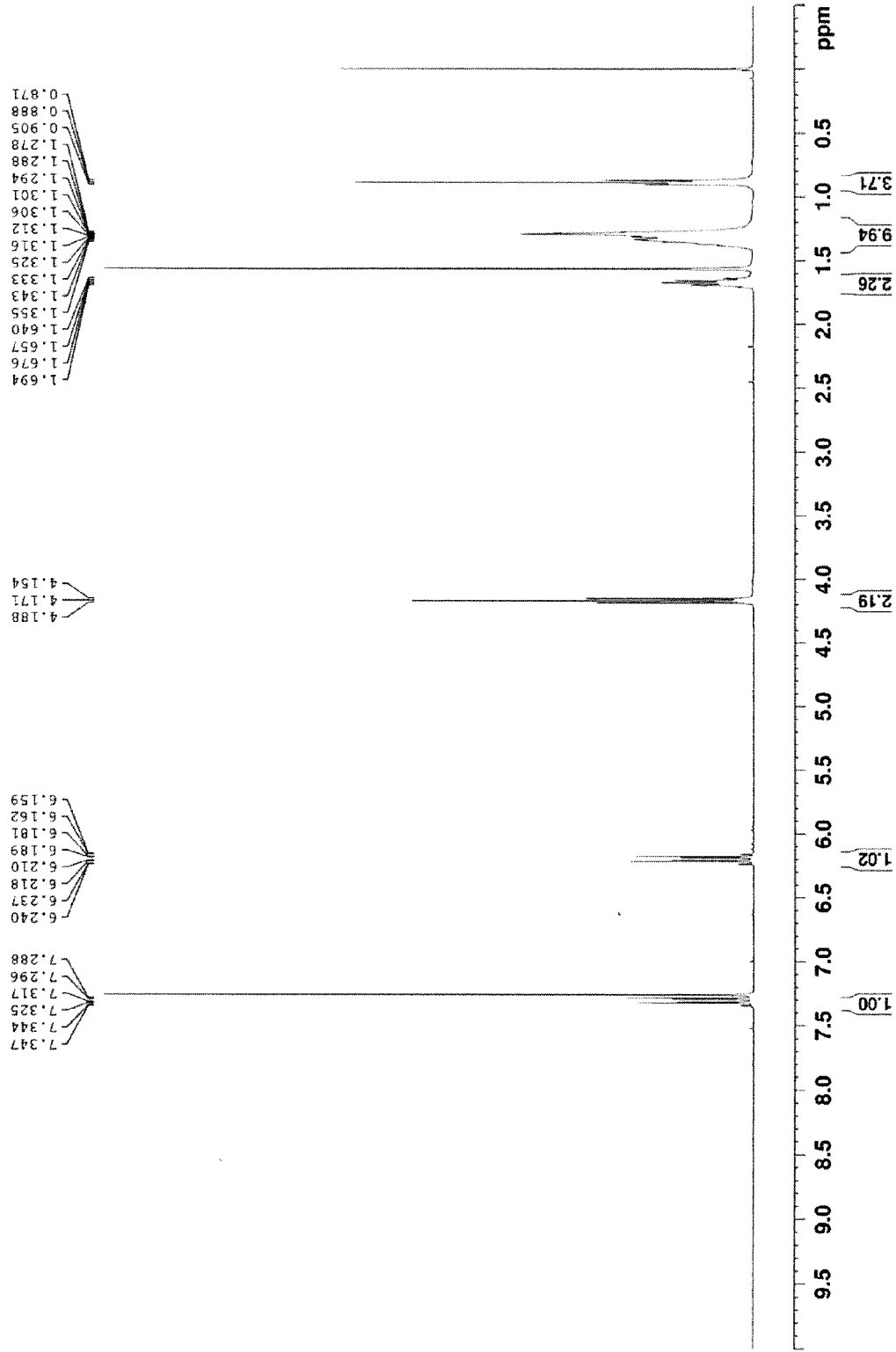
FIG. 9 shows $^1$H NMR data of diheptylgalactarate obtained in Example 4.
Figure 10:
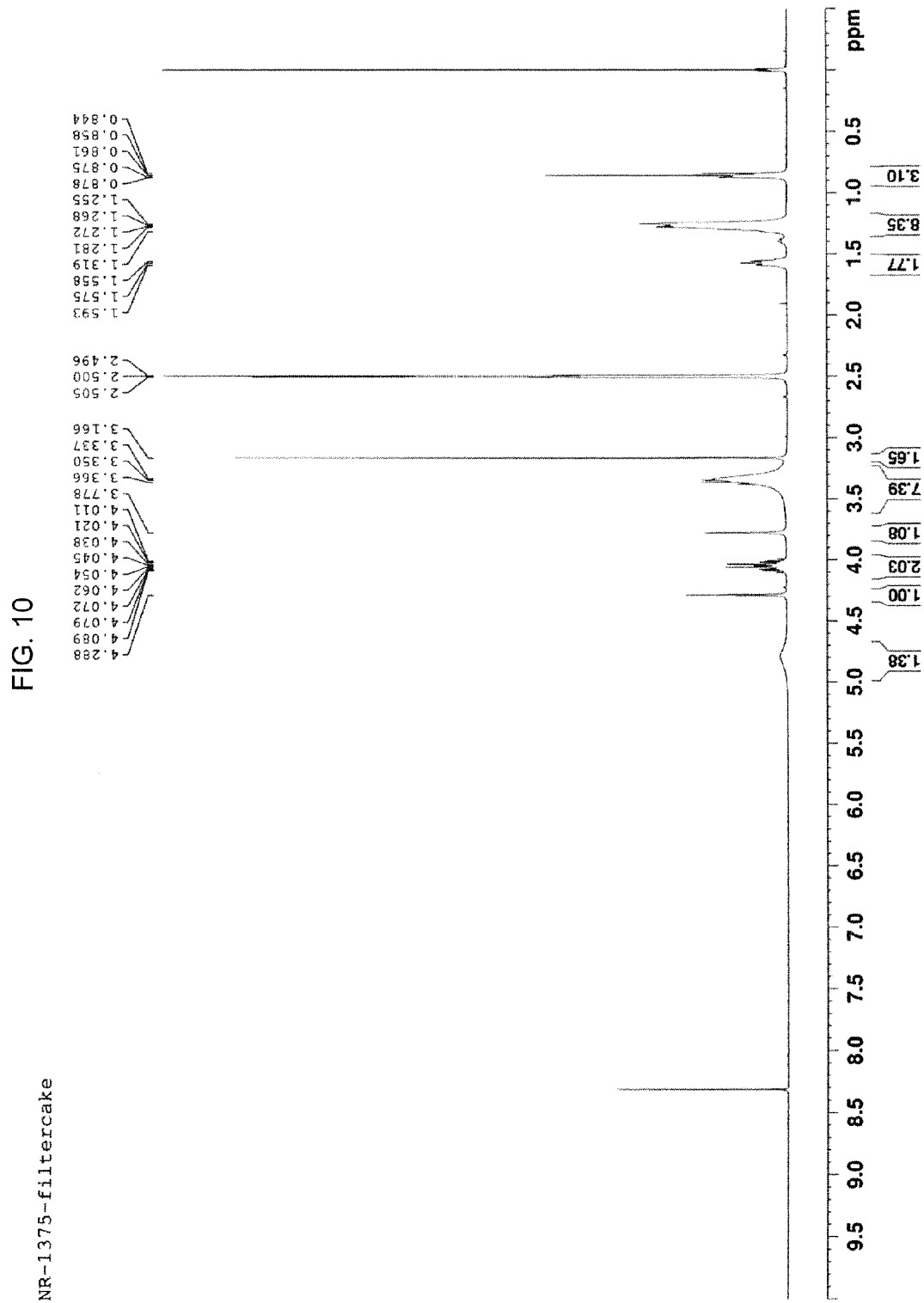
FIG. 10 shows $^1$H NMR data of the product obtained in Comparative Example 1.
Figure 11:
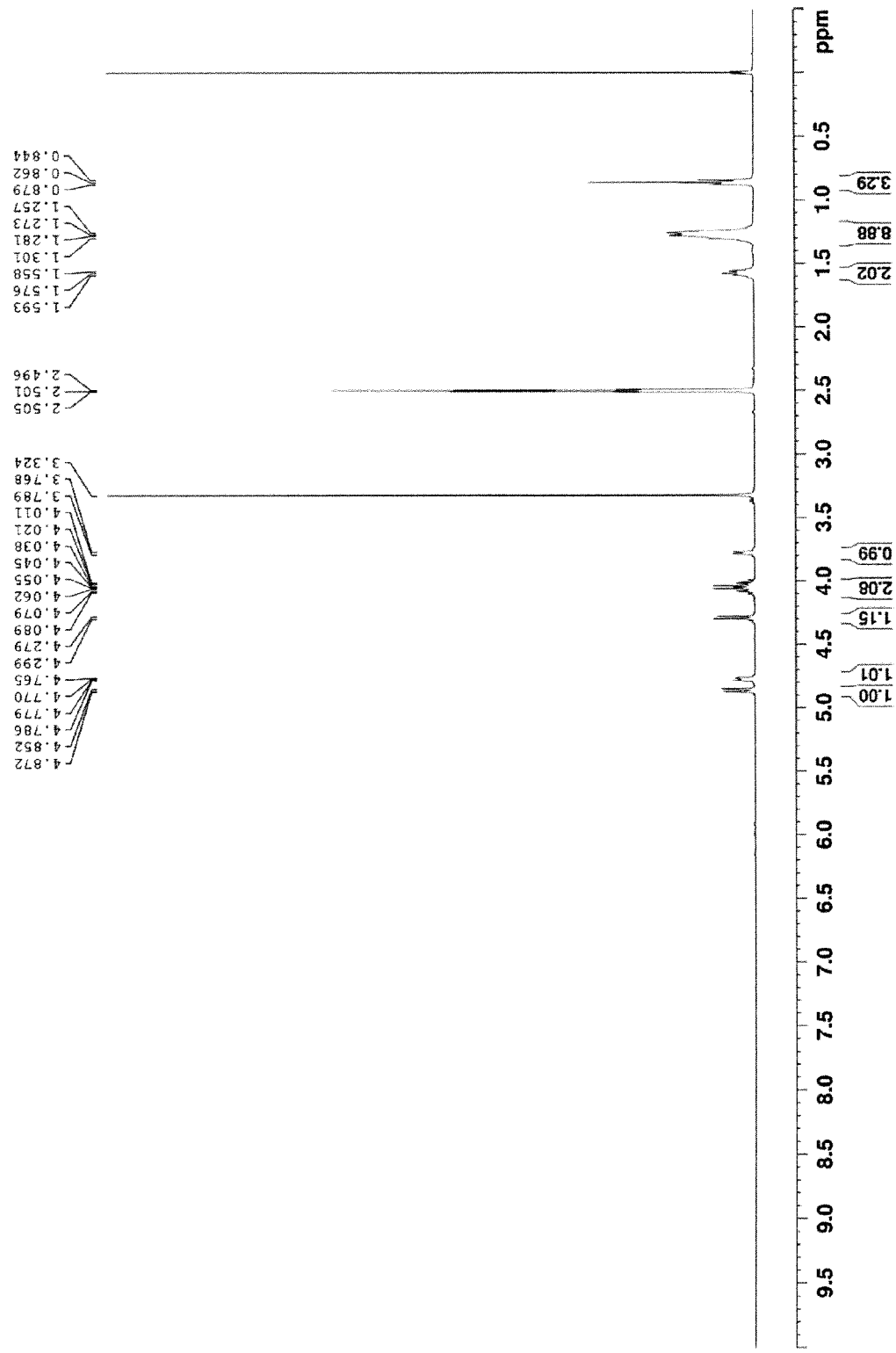
FIG. 11 shows $^1$H NMR data of the product obtained in Comparative Example 2.
Figure 12:
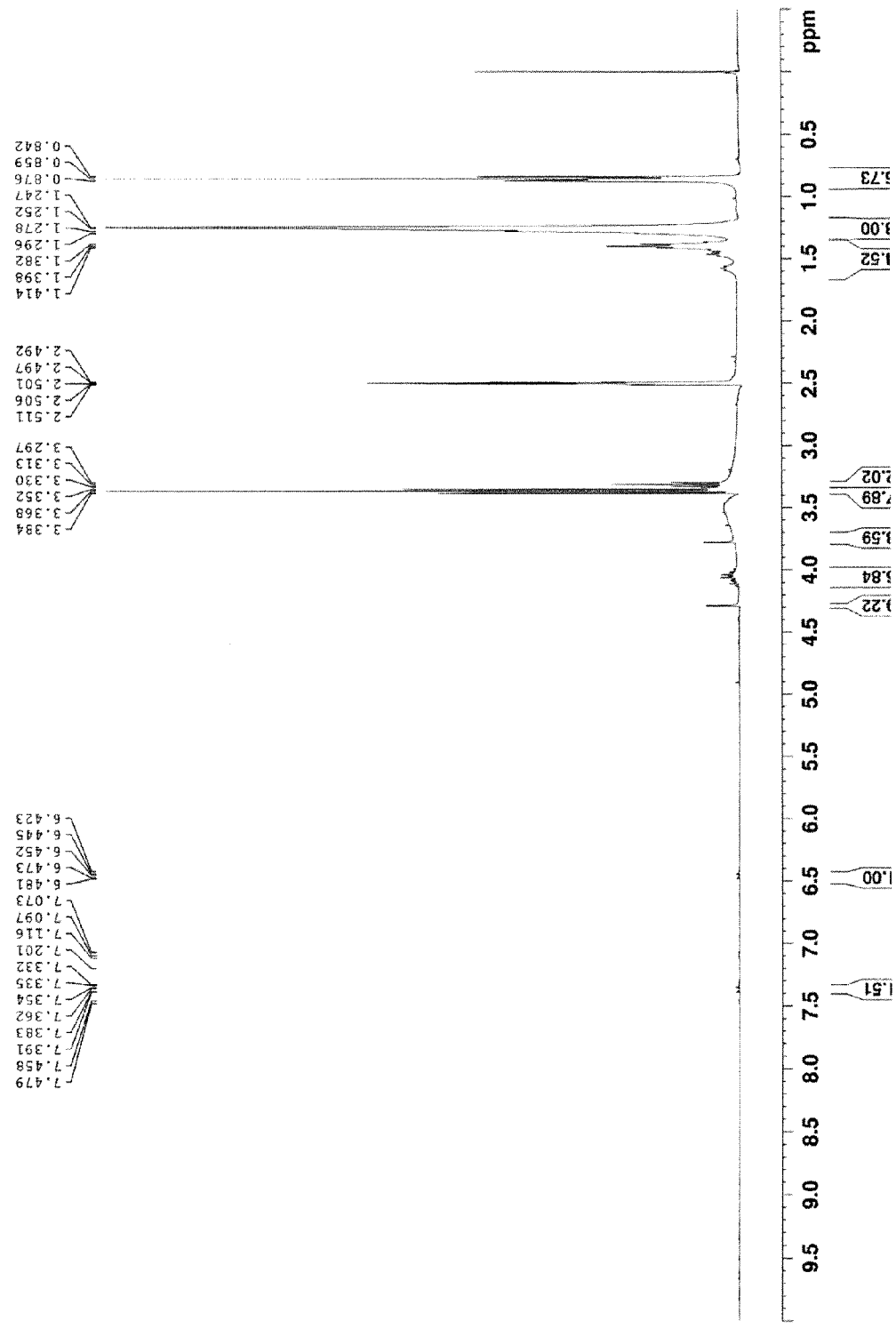
FIG. 12 shows $^1$H NMR data of the product obtained in Comparative Example 3.
Figure 13:
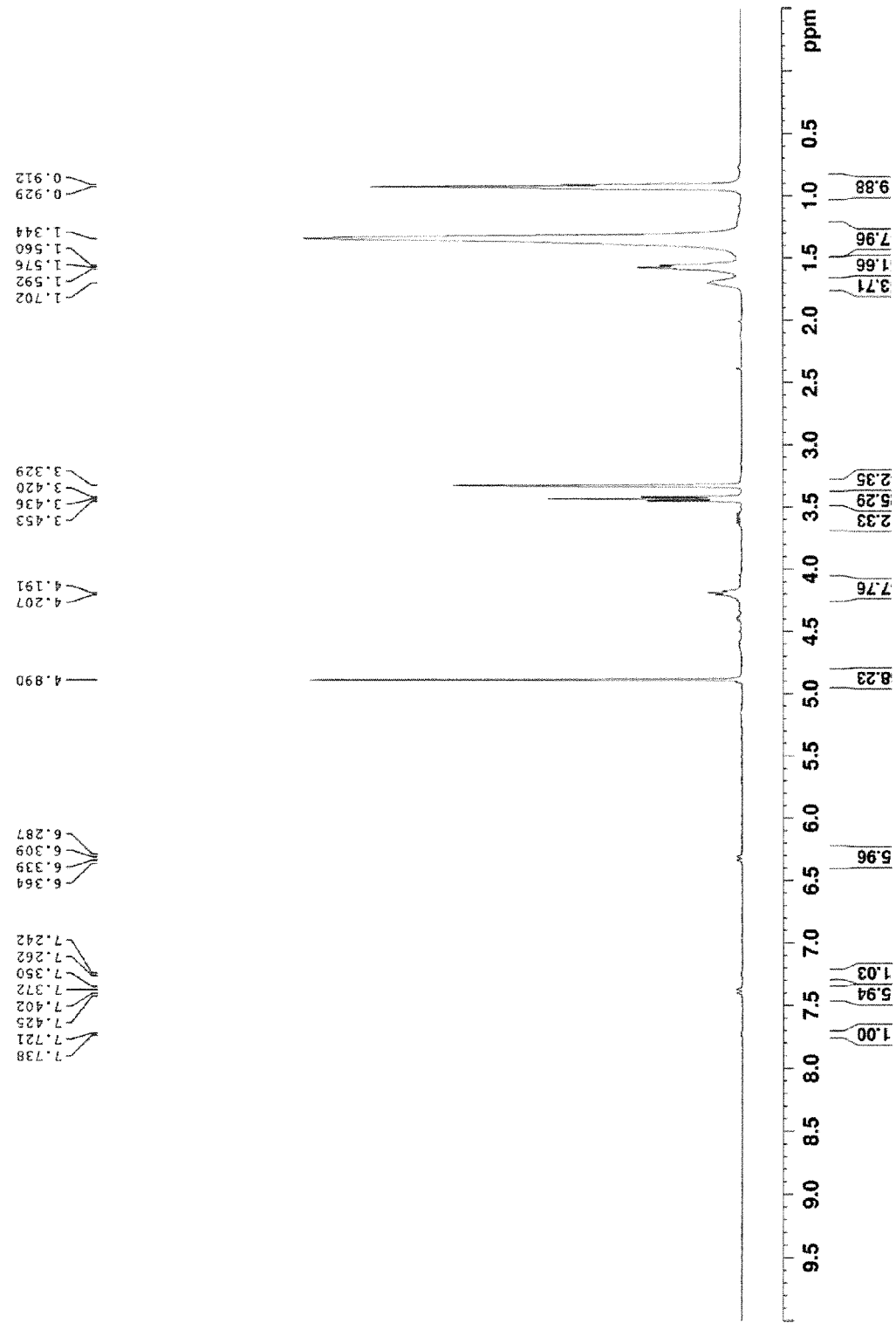
FIG. 13 shows $^1$H NMR data of the product obtained in Comparative Example 4.
Figure 14:
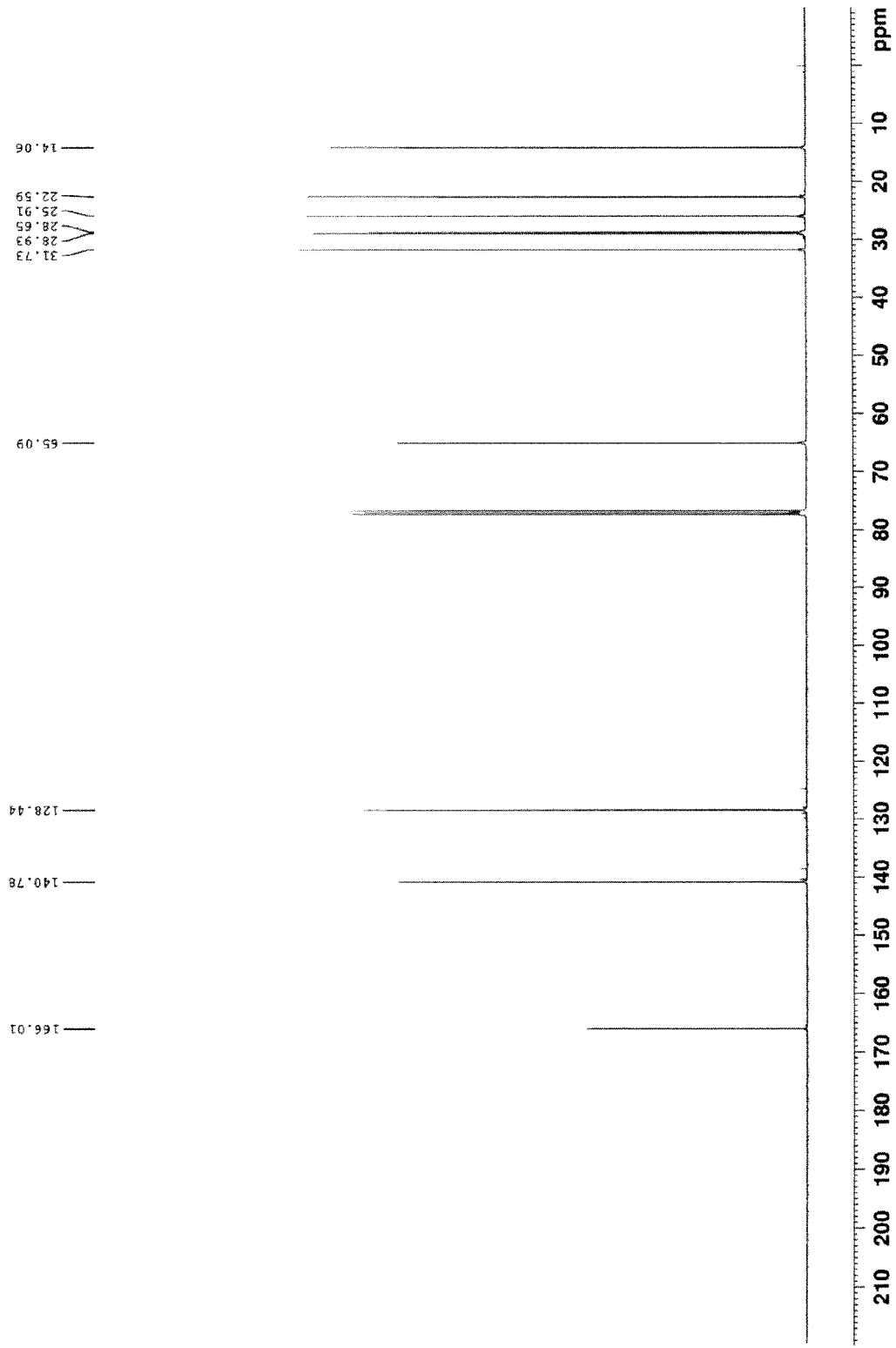
FIG. 14 shows $^{13}$C NMR data of diheptylgalactarate obtained in Example 1.
Figure 15:
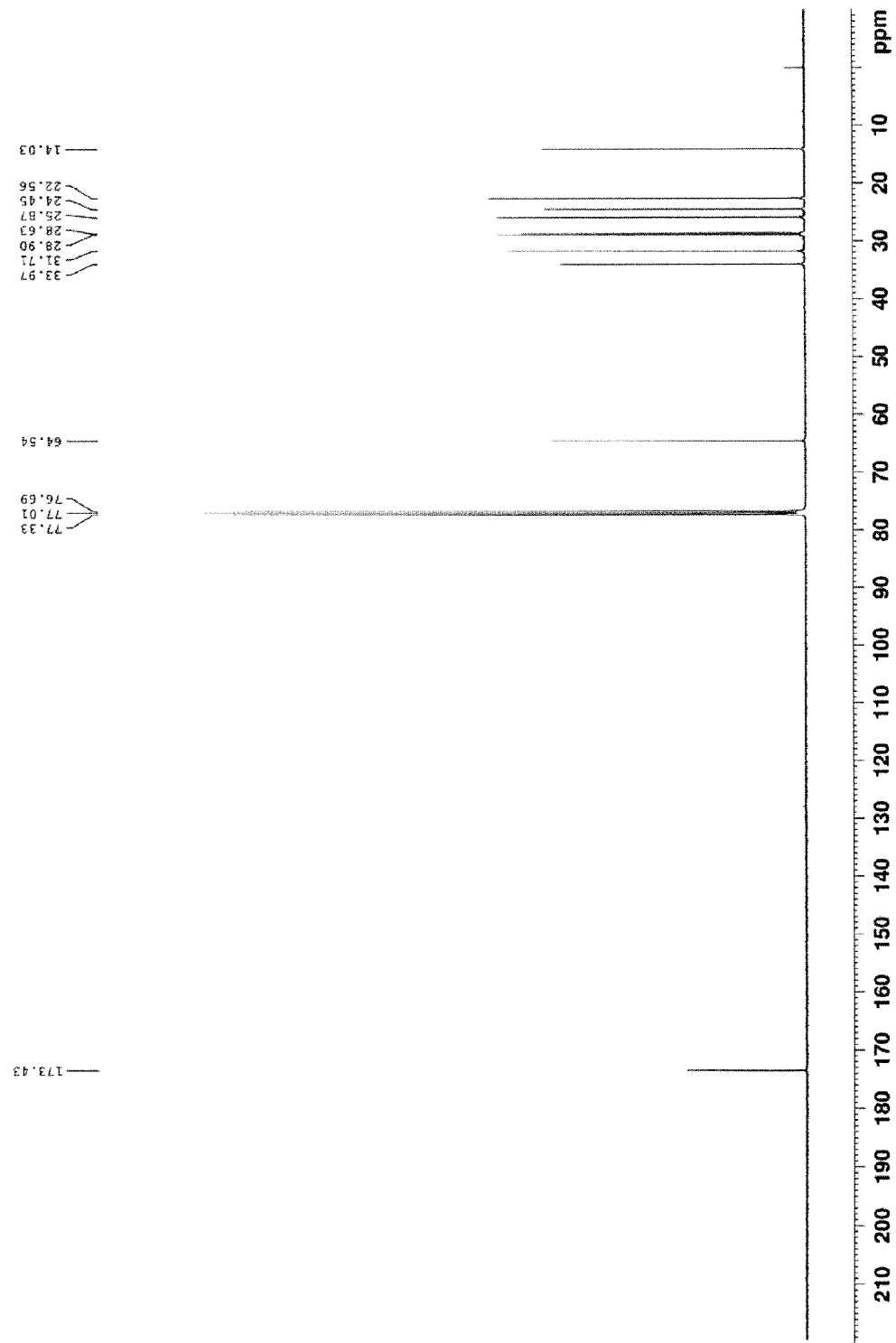
FIG. 15 shows $^{13}$C NMR data of diheptyladipate obtained in Example 1.
Figure 16:
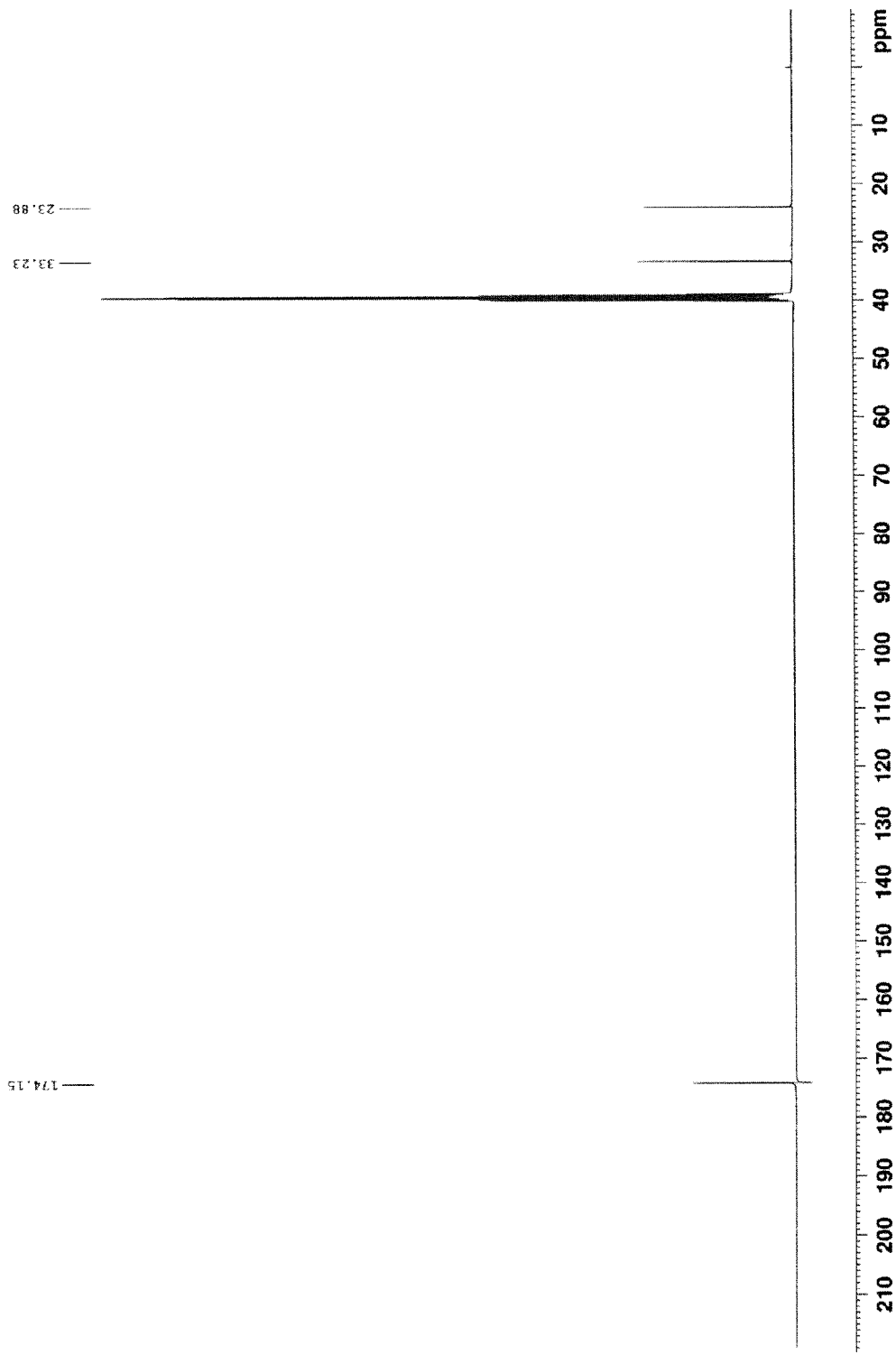
FIG. 16 shows $^1$H NMR data of adipic acid obtained in Example 1.

The present disclosure is further explained in more detail with reference to the following examples. These examples, however, should not be interpreted as limiting the scope of the present disclosure in any manner. FIG. 1 shows a reaction scheme when using galactaric acid as a starting material according to the present disclosure. FIG. 2 shows $^1$H NMR data of diheptylgalactarate obtained in Example 1. FIG. 3 shows $^1$H NMR data of diheptyladipate obtained in Example 1. FIG. 4 shows $^1$H NMR data of adipic acid obtained in Example 1. FIG. 5 shows $^1$H NMR data of diheptylgalactarate obtained in Example 2. FIG. 6 shows $^1$H NMR data of diheptyladipate obtained in Example 2. FIG. 7 shows $^1$H NMR data of adipic acid obtained in Example 2. FIG. 8 shows $^1$H NMR data of diheptylgalactarate obtained in Example 3. FIG. 9 shows $^1$H NMR data of diheptylgalactarate obtained in Example 4. FIG. 10 shows $^1$H NMR data of the product obtained in Comparative Example 1. FIG. 11 shows $^1$H NMR data of the product obtained in Comparative Example 2. FIG. 12 shows $^1$H NMR data of the product obtained in Comparative Example 3. FIG. 13 shows $^1$H NMR data of the product obtained in Comparative Example 4. FIG. 14 shows $^{13}$C NMR data of diheptylgalactarate obtained in Example 1. FIG. 15 shows $^{13}$C NMR data of diheptyladipate obtained in Example 1. FIG. 16 shows $^1$H NMR data of adipic acid obtained in Example 1.

Hereinafter, a process synthetic process of adipic acid will be described in detailed with reference to the accompanying drawings and examples.

(1) Preparation of Intermediate Through Deoxydehydration (DODH) Reaction

Step (a) of the disclosed process for synthesizing adipic acid is the step of preparing an intermediate of adipic acid through deoxydehydration (DODH) reaction. More specifically, the step includes using glucaric acid or galataric acid as a starting material, and adding rhenium and acid catalyst into a reaction solvent to prepare an intermediate of adipic acid.

The reaction solvent used in the step (a) may be an alcohol, such as butanol, heptanol, or 1-heptanol. Using butanol or heptanol as the reaction solvent for the step (a) has advantageous effects in terms of (i) lower costs relative to other solvents (e.g., 3-pentanol: 300,000 KRW (about 275 USD) per liter v. butanol: 10,000 KRW (about 9.1 USD) and heptanol: 100,000 KRW (about 91 USD)), (ii) ease of recycling, and ready supply, and (iii) high production yield of adipic acid.

Further, glucaric acid or galactaric acid used in the step (a) as a starting material may be obtained by a conventional preparation method, or commercially available glucaric acid or galactaric acid may also be used, but not limited thereto. Glucaric acid or galactaric acid may be prepared by a conventional method through the oxidation reaction of glucose or galactose derived from biomass, specifically, plant or marine resources.

The concentration of glucaric acid or galactaric acid used herein may be 0.01 M to 0.2 M. If the amount of glucaric acid or galactaric acid is less than 0.01 M, the economic efficiency of the process will be degraded, and if the concentration exceeds 0.2 M, the DODH reaction will barely be conducted, therefore the galactaric acid will be obtained by the esterification reaction only, and the conversion rate will decline.

Step (a) of the disclosed process provides a double bond by removing two (2) hydroxyl groups of glucaric acid or galactaric acid through the DODH reaction, with a catalyst, specifically the rhenium catalyst. An example of the rhenium catalyst used in the present disclosure is rhenium oxide (Rhenium(VII) oxide, $Re_2O_7$) and oxorhenium compounds ($L_xReO_y$, (wherein, L is amine, halogen, phenylsilyl, phosphine, $C_{1-10}$ alkoxy, $C_{1-10}$ alkyl or COOR (R is $C_{1-10}$ alkyl), x+y is an integer of 0 to 7); the catalyst selected from the group consisting of methyltrioxorhenium

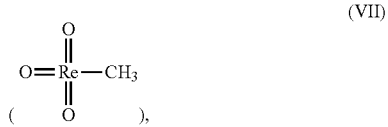

(VII)

Rhenium(VII) oxide, $Re_2O_7$, trioxo(triphenylsilyloxy)rhenium

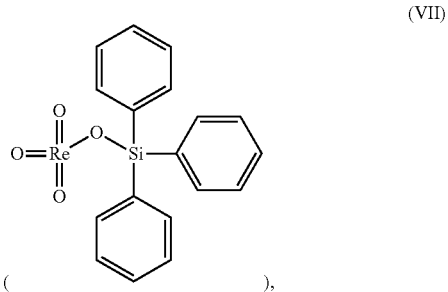

(VII)

and the mixture thereof; or methyltrioxorhenium.

The molar ratio of glucaric acid or galactaric acid:rhenium catalyst used in the step (a) may be 1:0.01 to 0.2.

If the molar ratio is less than 1:0.01, the reaction conversion rate will decline, and if the molar ratio exceeds 1:0.2, the economic efficiency is degraded and side reactions will occur.

The acid catalyst used in the step (a) facilitates the dehydration reaction of the hydroxyl groups in glucaric acid or galactaric acid.

Examples of the acid catalyst are organic and non-organic acids, including Amberlyst 15, 2,4-dinitrosulfonic acid, sulfuric acid, trifluoromethanesulfonic acid and para-toluenesulfonic acid. The molar ratio of glucaric acid or galactaric acid:acid catalyst used in step (a) may be 1:0.05 to 2.

If the molar ratio is less than 1:0.05, the reaction efficiency will decline, and if the molar ratio exceeds 1:2, side reactions such as cyclization will occur.

Further, as described above, the starting material (glucaric acid or galactaric acid), rhenium catalyst, and acid catalyst are added to the reaction solvent, and reacted together at a proper temperature for a proper reaction time, then separated and purified with a conventional method (e.g., purification with silica column) to obtain glucaric acid ester or galactaric acid ester as an intermediate of adipic acid. In one embodiment, the reaction temperature ranges from 100 to 200° C., and the reaction time is 12 to 24 hours.

The intermediate of adipic acid may vary according to the reaction solvent. Intermediates may include diheptyl galactarate or dibutyl galactarate, as galactaric acid esters.

In one specific embodiment of the present disclosure, 20 ml of 1-heptanol, 1 mmol of galactaric acid, 0.05 mmol of methyltrioxorhenium catalyst, and 0.05 mmol of para-toluenesulfonic acid were poured into a 50 cc reactor. The temperature in the reactor was then raised to 150° C. and the reaction was performed for 12 hours, maintaining the reactor temperature at 150° C. to obtain diheptyl galactarate.

Figure 17:
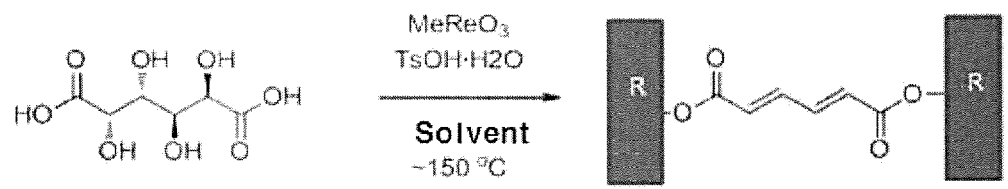
FIG. 17 shows a deoxydehydration reaction scheme by catalytic reaction of galactaric acid.
Figure 18:
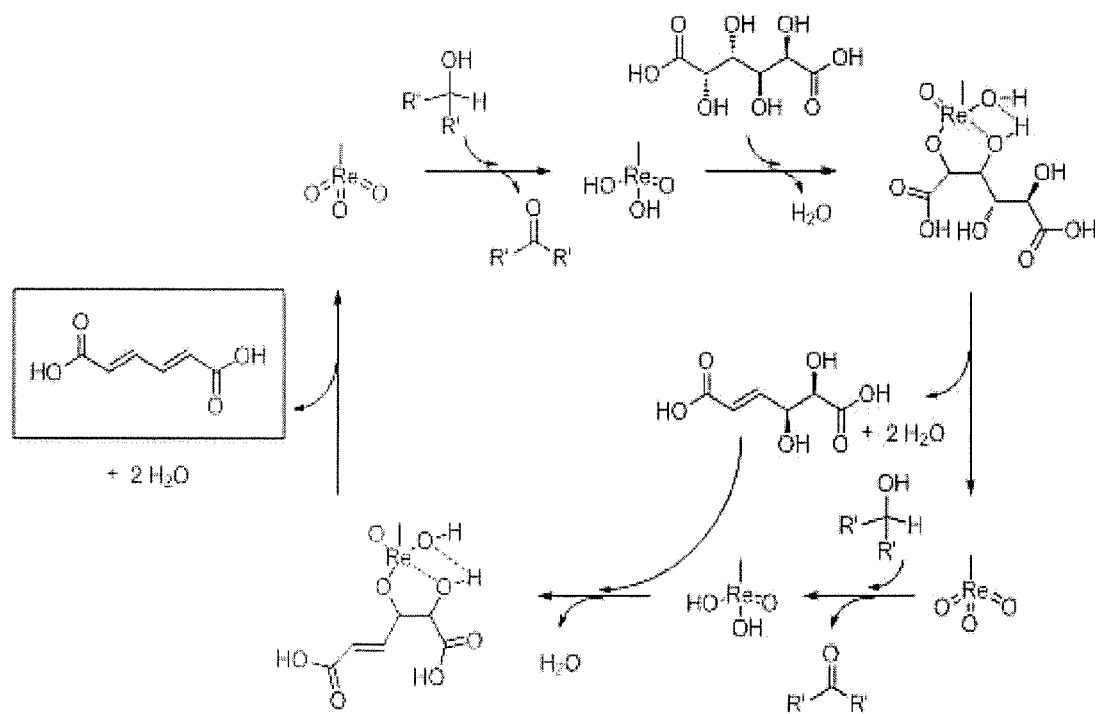
FIG. 18 shows a reaction mechanism for preparing an intermediate of adipic acid through a deoxydehydration reaction.

The step (a) of the inventive process is shown in FIG. 17, which illustrates Reaction Scheme 1 (DODH reaction scheme by catalytic reaction of galactaric acid), and FIG. 18, which illustrates Reaction Scheme 2 (reaction mechanism), but it is not limited by these illustrations.

(2) Preparation of Adipic Acid from an Intermediate

Step (b) of the inventive process for synthesizing adipic acid is the step of preparing adipic acid as a final product from the intermediate obtained in the step (a), more specifically, subjecting glucaric acid ester or galactaric acid ester (the intermediate obtained in the step a)) to a hydrogenation reaction with a precious metal catalyst in a proper reaction solvent, then hydrolyzing the product of this reaction to obtain adipic acid.

The reaction solvent used in the step (b) may be useful as far as dissolving the reactant and having high hydrogen solubility. The reaction solvent may be one or more solvents selected from the group consisting of alcohols, chloroform, hexane, ethyl acetate, dichloromethane, acetonitrile, and ethyl acetate, but not limited thereto. The reaction solvent may be used in amounts such that the intermediate solution has a concentration ranging from 0.1 M to 1 M.

The hydrogenation catalyst used in the step (b) may be a precious metal catalyst, specifically, aluminum, silica, or carbon-supported platinum or palladium catalyst. Hydrogenation catalysts include Pd/C or Pt/C. The hydrogenation catalyst is used to convert a double bond of the intermediate obtained from step (a) into a single bond. The weight ratio of the reactant (intermediate):the hydrogenation catalyst may be 1:0.05 to 0.3. If the weight ratio is less than 1:0.05, the reaction efficiency will decline, and if it exceeds 1:0.3, the economic efficiency will be degraded.

Hydrogen pressure for hydrogenation reaction may be atmospheric pressure to 30 bar, and reaction temperature may range from room temperature to 70° C. If the reaction temperature exceeds 70° C., side reactions may occur.

Then, the ester group of the reactant obtained from the hydrogenation reaction may be hydrolyzed under acidic or basic conditions to produce adipic acid as the final product. A proper acidifying agent, such as hydrochloric acid (which may be conc. hydrochloric acid), may be used to form the acidic condition, and NaOH may be used to form the basic condition.

Figure 19:
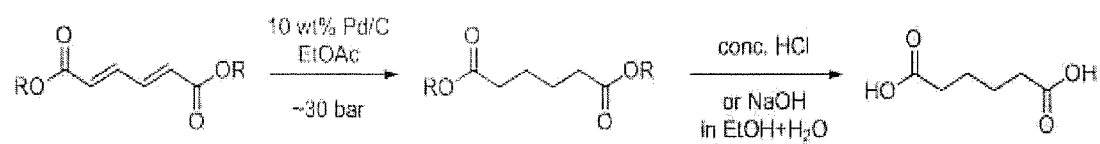
FIG. 19 shows a reaction scheme and reaction mechanism for preparing adipic acid from an intermediate.

One exemplified reduction reaction scheme and reaction mechanism of the step (b) (using diheptylgalactarate as an intermediate) is shown in FIG. 19, which illustrates Reaction Scheme 3, but not limited thereto. However, the same reaction scheme and reaction mechanism may be employed when using another intermediate of the present disclosure with the exception that the two (2) terminal groups bound to the oxygen atoms will change according to the intermediate.

In one specific example of the present disclosure, the steps (a) and (b) were performed in consecutive order, and produced a final product of adipic acid (white particles, melting point: 151° C.) via intermediates diheptylgalactarate or dibutylgalactarate (white particles, melting point: 58° C.).

The present disclosure provides for an environmentally-friendly synthesis of adipic acid from a biomass such as plant or marine resources, in contrast with the conventional method that uses petrochemical materials. Further, the present disclosure provides adipic acid with high yield and low costs relative to the conventional synthetic procedure.

EXAMPLES

Example 1

As described in Table 1, galactaric acid, the starting material, was poured into a reactor at a concentration of 0.05M, using 1-heptanol as a solvent. Methyltrioxorhenium was added as a catalyst at 1:0.05 molar ratio of galactaric acid:methyltrioxorhenium. Then, para-toluenesulfonic acid was added to the reactor at a concentration of 1:0.05 molar ratio of galactaric acid:para-toluenesulfonic acid.

The reaction was performed for 12 hours, maintaining 150° C. of the reactor.

After the reaction was terminated, the reaction product was separated from the remaining catalyst, and the produced diheptylgalactarate was confirmed by NMR analysis (Bruker AVIII400 Instrument) (FIG. 2 and FIG. 14). The NMR spectrum was measured by dissolving TMS (trimethylsilane) in $CDCl_3$ as an internal standard (1H at 400 MHz).

$^1H$ NMR ($CDCl_3$) δ 7.32-7.29 (m, 2H), 6.24-6.16 (m, 2H), 4.17 (t, J=6.8, 4H), 1.69-1.66 (m, 4H), 1.39-1.29 (m, 16H), 0.91-0.87 (m, 6H)

$^{13}C$ NMR ($CDCl_3$) δ66.0, 140.8, 128.4, 65.1, 31.7, 28.9, 28.7, 25.9, 22.6, 14.1

Then, the reaction product was dissolved in ethylacetate, Pd/C was added containing an amount of 10 wt % of Pd with respect to the reaction product and hydrogen gas. The reaction was carried out at 30 bar for 24 hours. After the reaction was terminated, the product of this reaction was separated from the remaining catalyst, and the produced diheptyladipate was confirmed by NMR analysis (Bruker AVIII400 Instrument) (FIGS. 3 and 15). The NMR spectrum was measured by dissolving TMS (trimethylsilane) in $CDCl_3$ as an internal standard ($^1H$ at 400 MHz).

$^1H$ NMR ($CDCl_3$) δ 4.17 (t, J=6.8, 4H), 2.35-2.30 (m, 4H), 1.69-1.58 (m, 8H), 1.36-1.29 (m, 16H) 0.91-0.87 (m, 6H)

$^{13}C$ NMR ($CDCl_3$) δ73.4, 64.5, 34.0, 31.7, 28.9, 28.6, 25.9, 24.5, 22.6, 14.0

The product was refluxed at a high temperature in the presence of hydrochloric acid and then the remaining hydrochloric acid was removed. Adipic acid synthesis was confirmed by performing NMR analysis (Bruker AVIII400 Instrument) and FT-IR Analysis (Agilent Technologies Cary 600) (FIGS. 4 and 16). The NMR spectrum was measured by dissolving TMS (trimethylsilane) in DMSO as an internal standard ($^1H$ at 400 MHz).

$^1H$ NMR (DMSO-$d_6$) δ 12.0 (bs, 2H), 2.23-2.09 (m, 4H), 1.52-1.48 (m, 4H)

$^{13}C$ NMR (DMSO-$d_6$) δ174.2, 33.2, 23.9

FT-IR (equipped with ATR accessory) 1689 $cm^{-1}$

Example 2

As described in Table 1, galactaric acid, the starting material, was poured into a reactor at a concentration of 0.05M to 1-heptanol as a solvent. Methyltrioxorhenium as a catalyst was added at a 1:0.05 molar ratio of galactaric acid:methyltrioxorhenium. Then, para-toluenesulfonic acid was added to the reactor to be a concentration of 1:0.05 molar ratio of galactaric acid:para-toluenesulfonic acid.

The reaction was performed for 12 hours, maintaining 150° C. of the reactor.

After the reaction was terminated, the reaction product was separated from the remaining catalyst, and the produced diheptylgalactarate was confirmed by NMR analysis (Bruker AVIII400 Instrument) (FIG. 5). The NMR spectrum was measured by dissolving TMS (trimethylsilane) in $CDCl_3$ as an internal standard (1H at 400 MHz).

$^1H$ NMR ($CDCl_3$) δ 7.32-7.29 (m, 2H), 6.24-6.16 (m, 2H), 4.17 (t, J=6.8, 4H), 1.69-1.66 (m, 4H), 1.39-1.29 (m, 16H), 0.91-0.87 (m, 6H)

$^{13}C$ NMR ($CDCl_3$) δ66.0, 140.8, 128.4, 65.1, 31.7, 28.9, 28.7, 25.9, 22.6, 14.1

Then, the reaction product was dissolved in ethylacetate, Pd/C was added containing an amount of 10 wt % Pd with respect to the reaction product and hydrogen gas. The reaction was carried out at 30 bar for 24 hours. After the reaction was terminated, the product of this reaction was separated from the remaining catalyst, and the produced diheptyladipate was confirmed by NMR analysis (Bruker AVIII400 Instrument) (FIG. 6). The NMR spectrum was measured by dissolving TMS (trimethylsilane) in $CDCl_3$ as an internal standard ($^1H$ at 400 MHz).

$^1H$ NMR ($CDCl_3$) δ 4.17 (t, J=6.8, 4H), 2.35-2.30 (m, 4H), 1.69-1.58 (m, 8H), 1.36-1.29 (m, 16H) 0.91-0.87 (m, 6H)

$^{13}C$ NMR ($CDCl_3$) 6173.4, 64.5, 34.0, 31.7, 28.9, 28.6, 25.9, 24.5, 22.6, 14.0

The product was refluxed for 12 hours in a mixed solution of methanol and water (at a volumetric ratio of 1:2) at a high temperature in the presence of NaCl and then the remaining methanol and water were removed. The crystalline product was formed by making the acid condition with 1N hydrochloric acid solution, and was separated by filtration. The produced adipic acid was confirmed by performing NMR analysis (Bruker AVIII400 Instrument) and FT-IR Analysis (Agilent Technologies Cary 600) (FIG. 7). The NMR spectrum was measured by dissolving TMS (trimethylsilane) in DMSO as an internal standard ($^1H$ at 400 MHz).

$^1H$ NMR (DMSO-$d_6$) δ 12.0 (bs, 2H), 2.23-2.09 (m, 4H), 1.52-1.48 (m, 4H)

$^{13}C$ NMR (DMSO-$d_6$) δ74.2, 33.2, 23.9

FT-IR (equipped with ATR accessory) 1689 $cm^{-1}$

Example 3

According to the composition presented in Table 1, galactaric acid as a starting material was poured to a reactor at a concentration of 0.1M to 1-heptanol as a solvent and methyltrioxorhenium as a catalyst was added at 1:0.05 molar ratio of galactaric acid:methyltrioxorhenium. Then, para-toluenesulfonic acid was added to the reactor to be a concentration of 1:0.05 molar ratio of galactaric acid:para-toluenesulfonic acid.

The reaction was performed for 12 hours, maintaining 150° C. of the reactor.

After the reaction was terminated, the reaction product was separated from the remaining catalyst, and the produced diheptylgalactarate was confirmed by NMR analysis (Bruker AVIII400 Instrument) (FIG. 8). The NMR spectrum was measured by dissolving TMS (trimethylsilane) in $CDCl_3$ as an internal standard (1H at 400 MHz).

$^1$H NMR (CDCl$_3$) δ 7.32-7.29 (m, 2H), 6.24-6.16 (m, 2H), 4.17 (t, J=6.8, 4H), 1.69-1.66 (m, 4H), 1.39-1.29 (m, 16H), 0.91-0.87 (m, 6H)

$^{13}$C NMR (CDCl$_3$) δ66.0, 140.8, 128.4, 65.1, 31.7, 28.9, 28.7, 25.9, 22.6

Then, the reaction product was dissolved in ethylacetate, Pd/C was added containing an amount of 10 wt % Pd with respect to the reaction product and hydrogen gas. The reaction was carried out at 30 bar for 24 hours. After the reaction was terminated, the product of this reaction was separated from the remaining catalyst, and the produced diheptyladipate was confirmed by NMR analysis (Bruker AVIII400 Instrument) (FIGS. 3 and 15). The NMR spectrum was measured by dissolving TMS (trimethylsilane) in CDCl$_3$ as an internal standard ($^1$H at 400 MHz).

$^1$H NMR (CDCl$_3$) δ 4.17 (t, J=6.8, 4H), 2.35-2.30 (m, 4H), 1.69-1.58 (m, 8H), 1.36-1.29 (m, 16H) 0.91-0.87 (m, 6H)

$^{13}$C NMR (CDCl$_3$) δ73.4, 64.5, 34.0, 31.7, 28.9, 28.6, 25.9, 24.5, 22.6, 14.0

The product was refluxed for 12 hours in a mixed solution of methanol and water (at a volumetric ratio of 1:2) at a high temperature in the presence of NaCl and then the remaining methanol and water were removed. The crystal was formed under acidic conditions using 1N hydrochloric acid solution, and was separated by filtration. The produced adipic acid was confirmed by performing NMR analysis (Bruker AVIII400 Instrument) and FT-IR Analysis (Agilent Technologies Cary 600). The NMR spectrum was measured by dissolving TMS (trimethylsilane) in DMSO as an internal standard ($^1$H at 400 MHz).

$^1$H NMR (DMSO-d$_6$) δ 12.0 (bs, 2H), 2.23-2.09 (m, 4H), 1.52-1.48 (m, 4H)

$^{13}$C NMR (DMSO-d$_6$) δ174.2, 33.2, 23.9

FT-IR (equipped with ATR accessory) 1689 cm$^{-1}$

Example 4

According to the composition presented in Table 1, galactaric acid as a starting material was poured to a reactor at a concentration of 0.05M to 1-heptanol as a solvent and methyltrioxorhenium as a catalyst was added at a concentration of 1:0.05 molar ratio of galactaric acid:methyltrioxorhenium. Then, para-toluenesulfonic acid was added to the reactor to a concentration of 1:0.05 molar ratio of galactaric acid:para-toluenesulfonic acid.

The reaction was performed for 12 hours, maintaining 120° C. of the reactor.

After the reaction was terminated, the reaction product was separated from the remaining catalyst, and the produced diheptylgalactarate was confirmed by NMR analysis (Bruker AVIII400 Instrument) (FIG. 9). The NMR spectrum was measured by dissolving TMS (trimethylsilane) in CDCl$_3$ as an internal standard (1H at 400 MHz).

$^1$H NMR (CDCl$_3$) δ 7.32-7.29 (m, 2H), 6.24-6.16 (m, 2H), 4.17 (t, J=6.8, 4H), 1.69-1.66 (m, 4H), 1.39-1.29 (m, 16H), 0.91-0.87 (m, 6H)

$^{13}$C NMR (CDCl$_3$) 6166.0, 140.8, 128.4, 65.1, 31.7, 28.9, 28.7, 25.9, 22.6, 14.1

Then, the reaction product was dissolved in ethylacetate, Pd/C was added containing an amount of 10 wt % Pd with respect to the reaction product and hydrogen gas. The reaction was carried out at 30 bar for 24 hours. After the reaction was terminated, the product of this reaction was separated from the remaining catalyst, and the produced diheptyladipate was confirmed by NMR analysis (Bruker AVIII400 Instrument). The NMR spectrum was measured by dissolving TMS (trimethylsilane) in CDCl$_3$ as an internal standard ($^1$H at 400 MHz).

$^1$H NMR (CDCl$_3$) δ 4.17 (t, J=6.8, 4H), 2.35-2.30 (m, 4H), 1.69-1.58 (m, 8H), 1.36-1.29 (m, 16H) 0.91-0.87 (m, 6H)

$^{13}$C NMR (CDCl$_3$) δ73.4, 64.5, 34.0, 31.7, 28.9, 28.6, 25.9, 24.5, 22.6, 14.0

The product was refluxed for 12 hours in a mixed solution of methanol and water (at a volumetric ratio of 1:2) at a high temperature in the presence of NaCl and then the remaining methanol and water were removed. The crystal was formed under acidic conditions using 1N hydrochloric acid solution, and was separated by filtration. The produced adipic acid was confirmed by performing NMR analysis (Bruker AVIII400 Instrument) and FT-IR Analysis (Agilent Technologies Cary 600). The NMR spectrum was measured by dissolving TMS (trimethylsilane) in DMSO as an internal standard ($^1$H at 400 MHz).

$^1$H NMR (DMSO-d$_6$) δ 12.0 (bs, 2H), 2.23-2.09 (m, 4H), 1.52-1.48 (m, 4H)

$^{13}$C NMR (DMSO-d$_6$) δ174.2, 33.2, 23.9

FT-IR (equipped with ATR accessory) 1689 cm$^{-1}$

Comparative Example 1

According to the composition presented in Table 1, galactaric acid as a starting material was poured into a reactor at a concentration of 0.05M to 1-heptanol as a solvent and para-toluenesulfonic acid was added at a concentration of 1:1 molar ratio of para-toluenesulfonic acid to galactaric acid.

The reaction was performed for 12 hours, maintaining 150° C. of the reactor.

After the reaction was terminated, the product was separated from the remaining catalyst, and was analyzed by NMR (Bruker AVIII400 Instrument). Diheptylgalactarate was not synthesized well (FIG. 10).

Comparative Example 2

According to the composition presented in Table 1, galactaric acid as a starting material was poured into a reactor at a concentration of 0.05M to 1-heptanol as a solvent and methyltrioxorhenium as a catalyst was added at 1:0.05 molar ratio of galactaric acid:methyltrioxorhenium. Then, Amberlyst 15 was added to the reactor to be a concentration of 1:1 molar ratio of galactaric acid:Amberlyst 15.

The reaction was performed for 12 hours, maintaining 80° C. of the reactor.

After the reaction was terminated, the product was separated from the remaining catalyst, and was analyzed by NMR (Bruker AVIII400 Instrument). Diheptylgalactarate was not synthesized well (FIG. 11).

Comparative Example 3

According to the composition presented in Table 1, galactaric acid as a starting material was poured into a reactor at a concentration of 0.05M to 1-heptanol as a solvent and methyltrioxorhenium was added as a catalyst at 1:0.05 molar ratio of galactaric acid:methyltrioxorhenium. Then, para-toluenesulfonic acid was added to the reactor at a concentration of 1:0.05 molar ratio of galactaric acid:para-toluenesulfonic acid.

The reaction was performed for 12 hours, maintaining 80° C. of the reactor.

After the reaction was terminated, the product was separated from the remaining catalyst, and was analyzed by NMR (Bruker AVIII400 Instrument). Diheptylgalactarate was not synthesized well (FIG. 12).

Comparative Example 4

According to the composition presented in Table 1, galactaric acid as a starting material was poured into a reactor at a concentration of 0.5M to 1-heptanol as a solvent and methyltrioxorhenium was added as a catalyst at 1:0.05 molar ratio of galactaric acid:methyltrioxorhenium. Then, para-toluenesulfonic acid was added to the reactor at concentration of 1:0.05 molar ratio of galactaric acid:para-toluenesulfonic acid.

The reaction was performed for 12 hours, maintaining 150° C. of the reactor.

After the reaction was terminated, the product was separated from the remaining catalyst, and was analyzed by NMR (Bruker AVIII400 Instrument). Diheptylgalactarate was not synthesized well (FIG. 13).

Then, the produced diheptylgalactarate was added to a reactor and the hydrogenation and hydrolysis reaction were carried out in ethyl acetate. Hydrogen gas and Pt or Pd catalyst were added under the specific conditions of Examples 1 to 4. The products were identified and analyzed using NMR (Bruker AVIII400 Instrument) and FT-IR (Agilent Technologies Cary 600). The NMR and FT-IR data, depicted in FIGS. 4 to 7 and 18, confirmed the synthesized adipic acid.

$^1$H NMR (DMSO-$d_6$) δ 12.0 (bs, 2H), 2.23-2.09 (m, 4H), 1.52-1.48 (m, 4H)

$^{13}$C NMR (DMSO-$d_6$) δ174.2, 33.2, 23.9

FT-IR (equipped with ATR accessory) 1689 cm$^{-1}$

Advantageous Effects

The novel synthetic process according to the present disclosure makes it possible to prepare adipic acid from a biomass such as plant or marine resources, which is environmentally friendly. Further, the present disclosure provides adipic acid with high yield and low costs by an even

TABLE 1

| Items | Examples | | | | Comparative Examples | | | |
| --- | --- | --- | --- | --- | --- | --- | --- | --- |
| | 1 | 2 | 3 | 4 | 1 | 2 | 3 | 4 |
| (A) | 0.05M | 0.05M | 0.10M | 0.05M | 0.05M | 0.05M | 0.05M | 0.5M |
| (B) | 1:0.05 | 1:0.05 | 1:0.05 | 1:0.05 | — | 1:0.05 | 1:0.05 | 1:0.05 |
| (C) | Para-toluene sulfonic acid | | | | | Amberlyst 15 | Para-toluene sulfonic acid | |
| | 1:0.05 | 1:0.05 | 1:0.05 | 1:0.05 | — | 1:0.05 | 1:0.05 | 1:0.05 |
| Reaction Temperature | 150° C. | 150° C. | 150° C. | 120° C. | 150° C. | 80° C. | 80° C. | 150° C. |
| Production of Diheptyl-3-yl galactarate | ○ | ○ | ○ | ○ | X | X | X | X |
| (D) hydrogenating catalyst | 10 wt % Pd/C 30 bar 24 hr | 10 wt % Pd/C 30 bar 24 hr | 10 wt % Pd/C 30 bar 24 hr | 10 wt % Pd/C 30 bar 24 hr | — | — | — | — |
| Production of adipic acid | ○ | ○ | ○ | ○ | — | — | — | — |

(A) Molar ratio of galactaric acid (Sigma-Aldrich (USA)):1-heptanol
(B) Molar ratio of galactaric acid (Sigma-Aldrich (USA)):methyltrioxorhenium
(C) Molar ratio of galactaric acid (Sigma-Aldrich (USA)):acid catalyst (Amberlyst 15 or Para-toluene sulfonic acid)
(D) The amount of Pd in the Pd/C catalyst, the pressure of hydrogen gas Experimental Example NMR Analysis NMR analysis was carried out to identify the components of products in Examples 1 to 4 and Comparative Examples 1 to 4. NMR spectra were analyzed with Bruker AVIII400 instrument, using TMS (trimethylsilane) dissolved in CDCl$_3$ or DMSO as an internal standard ($^1$H at 400 MHz) and ($^{13}$C at 100 MHz), respectively.

The following NMR data were obtained from the products of Examples 1 to 4.

As shown in Table 1, diheptylgalactarate in Examples 1 to 4 was synthesized by adding galactaric acid, para-toluene sulfonic acid, and rhenium catalyst to 1-heptanol, under specific temperature and catalyst conditions, compared to Comparative Examples 1 to 4.

$^1$H NMR (CDCl$_3$) δ 7.32-7.29 (m, 2H), 6.24-6.16 (m, 2H), 4.17 (t, J=6.8, 4H), 1.69-1.66 (m, 4H), 1.39-1.29 (m, 16H), 0.91-0.87 (m, 6H)

$^{13}$C NMR (CDCl$_3$) δ66.0, 140.8, 128.4, 65.1, 31.7, 28.9, 28.7, 25.9, 22.6, 14.1 simpler process than the conventional synthesizing process. Thus, the present disclosure could have huge ripple effects on the industry as a technology employing bio-adipic acid as a raw material for nylon 66, which is useful for the automobile industry.

What is claimed is:

1. A process for synthesizing adipic acid comprising steps of:
    a) adding glucaric acid or galactaric acid to a rhenium catalyst and an acid catalyst and heptanol as a reaction solvent; and
    b) subjecting glucaric acid ester or galactaric acid ester obtained from the step a) to a hydrogenation reaction with a precious metal catalyst, and hydrolyzing the ester obtained from this reaction to obtain adipic acid,
    wherein the rhenium catalyst of the step a) is one or more catalysts selected from the group consisting of rhenium oxide and L$_x$ReO$_y$, wherein L is amine, halogen, phenylsilyl, phosphine, C$_{1-10}$ alkoxy, C$_{1-10}$ alkyl or COOR (R is C$_{1-10}$ alkyl), x+y is an integer of 0 to 7;
    the acid catalyst of the step a) is one or more catalyst selected from the group consisting of Amberlyst 15, 2,4-dinitrosulfonic acid, sulfuric acid, benzene sulfonic acid, trifluoromethanesufonic acid, and para-toluenesulfonic acid;

the precious metal catalyst of the step b) is aluminum, silica, or carbon-supported Pt or Pd; and the step b) is performed in ethyl acetate as a solvent.

2. The process according to claim 1,
wherein the glucaric acid or the galactaric acid of the step a) is prepared by an oxidation reaction of glucose or galactose derived from plant resources or marine resources.

3. The process according to claim 1,
wherein the rhenium catalyst of the step a) is selected from the group consisting of rhenium oxide, methyl trioxorhenium, trioxo(triphenylsilyloxy)rhenium, and the mixture thereof.

4. The process according to claim 1,
wherein the concentration of the glucaric acid or the galactaric acid ranges from 0.01 to 0.2M.

5. The process according to claim 1,
wherein the molar ratio of the glucaric acid or the galactaric acid:the rhenium catalyst is 1:0.01 to 0.2.

6. The process according to claim 1,
wherein the molar ratio of the glucaric acid or the galactaric acid:the acid catalyst is 1:0.05 to 2.

7. The process according to claim 1,
wherein the step a) is performed at 100 to 200° C.

8. The process according to claim 1,
wherein the step a) is performed for 12 to 24 hours.

9. The process according to claim 1,
wherein the step a) further comprises separating and purifying the resulting glucaric acid ester or galataric acid ester.

10. The process according to claim 1,
wherein the glucaric acid ester or the galactaric acid ester is diheptyl galactarate or dibutyl galactarate.

11. The process according to claim 1,
wherein the weight ratio of the glucaric acid ester or the galactaric acid ester:the precious metal catalyst is 1:0.05 to 0.3.

12. The process according to claim 1,
wherein step b) is performed under atmospheric pressure to 30 bar.

13. The process according to claim 1,
wherein step b) is performed at a range of room temperature to 70° C.

* * * * *